United States Patent
Zhang et al.

(10) Patent No.: US 9,743,858 B2
(45) Date of Patent: Aug. 29, 2017

(54) MAGNETIC RESONANCE IMAGING APPARATUS AND A METHOD FOR DETERMINING TRIGGER TIMING OF CE-MRA SCAN

(71) Applicant: TOSHIBA MEDICAL SYSTEMS CORPORATION, Otawara-Shi (JP)

(72) Inventors: Lijun Zhang, Beijing (CN); Ye Liu, Beijing (CN); Kensuke Shinoda, Otawara (JP); Kiyomi Ooshima, Nasushiobara (JP)

(73) Assignee: Toshiba Medical Systems Corporation, Otawara-shi (JP)

( * ) Notice: Subject to any disclaimer, the term of this patent is extended or adjusted under 35 U.S.C. 154(b) by 403 days.

(21) Appl. No.: 13/684,418

(22) Filed: Nov. 23, 2012

(65) Prior Publication Data
US 2013/0137967 A1    May 30, 2013

(30) Foreign Application Priority Data

Nov. 25, 2011    (CN) .......................... 2011 1 0381985

(51) Int. Cl.
*A61B 5/055* (2006.01)
*A61B 5/026* (2006.01)
(Continued)

(52) U.S. Cl.
CPC ............ *A61B 5/055* (2013.01); *A61B 5/0263* (2013.01); *G01R 33/56* (2013.01); *G01R 33/563* (2013.01);
(Continued)

(58) Field of Classification Search
None
See application file for complete search history.

(56) References Cited

U.S. PATENT DOCUMENTS 6,167,293 A    12/2000  Chenevert et al.
6,489,486 B2   12/2002  Huber

FOREIGN PATENT DOCUMENTS

CN    101647699 A     2/2010
JP    2003-235827 A   8/2003
(Continued)

OTHER PUBLICATIONS

Doppler Ultrasound and Magnetic Resonance Imaging of Synovial Inflammation of the Hand in Rheumatoid Arthritis A Comparative Study by L. Terslev et al. pub. Arthritis & Rheumatism vol. 48, No. 9, Sep. 2003, pp. 2434-2441 DOI 10.1002/art.11245.*

(Continued)

*Primary Examiner* — Katherine Fernandez
*Assistant Examiner* — Michael Kellogg
(74) *Attorney, Agent, or Firm* — Oblon, McClelland, Maier & Neustadt, L.L.P.

(57) ABSTRACT

The present invention discloses an apparatus and a method for determining a trigger timing of a CE-MRA scan. The apparatus comprises: a blood flow velocity acquisition unit configured to acquire a blood flow velocity of a target vessel; and a trigger timing determination unit configured to determine the trigger timing for performing the CE-MAR scan on a CE-MRA scan region according to the blood flow velocity and a predetermined image acquisition condition during a monitoring scan. The apparatus and method take the blood flow velocity into consideration, and can determine the trigger timing of the CE-MRA scan automatically and accurately.

1 Claim, 14 Drawing Sheets

(51) Int. Cl.
  *G01R 33/563* (2006.01)
  *G01R 33/56* (2006.01)
(52) U.S. Cl.
  CPC .... *G01R 33/5635* (2013.01); *G01R 33/56316* (2013.01)

(56) References Cited

FOREIGN PATENT DOCUMENTS

| JP | 2009-297216 A | 12/2009 |
|---|---|---|
| WO | WO 03/034901 A2 | 5/2003 |

OTHER PUBLICATIONS

Estimation of kspace trajectories in spiral MRI by Hao Tan et al. pub. Magn Reson Med. Jun. 2009; 61(6): 1396-1404.*

Steady-state free precession imaging by Wikipedia, pub. online on Sep. 26, 2011 at https://en.wikipedia.org/w/index.php?title=Steadystate_free_precession_imaging&oldid=452543736.*

Fast low angle shot magnetic resonance imaging by Wikipedia, pub. online on Sep. 7, 2011 at https://en.wikipedia.org/w/index.php?title=Fast_low_angle_shot_magnetic_resonance_imaging&oldid=448966855.*

Cardiac gating with a pulse oximeter for dual energ imaging by N A Shkumat et al. pub. Oct. 14, 2008 • 2008 Institute of Physics and engineering in Medicine Physics in Medicine and Biology, vol. 53, No. 21.*

Relaxation (NMR) by Wikipedia, pub. online on Aug. 1, 2012 at https://en.wikipedia.org/w/index.php?title=Relaxation_(NMR)&oldid=505311371.*

Spin-lattice relaxation by Wikipedia, pub. online on Jun. 9, 2011 at https://en.wikipedia.org/w/index.php?title=Spin-lattice_relaxation&oldid=433455002.*

Spin-spin relaxation by Wikipedia, pub. online on Jun. 29, 2011 at https://en.wikipedia.org/w/index.php?title=Spin-spin_relaxation&oldid=436820171.*

Combined Office Action and Search Report issued Jul. 24, 2014 in Chinese Patent Application No. 201110381985.3 (with English translation).

Office Action issued Aug. 23, 2016 in Japanese Patent Application No. 2012-256693.

* cited by examiner

MAGNETIC RESONANCE IMAGING APPARATUS AND A METHOD FOR DETERMINING TRIGGER TIMING OF CE-MRA SCAN

CROSS-REFERENCE TO RELATED APPLICATION

This application is based upon and claims the benefit of priority from Chinese Patent Application No. 201110381985.3, filed on Nov. 25, 2011, the entire contents of which are incorporated herein by reference.

FIELD

The present invention relates to the technical field of Magnetic Resonance Imaging (MRI), and more particularly to an apparatus and a method for determining a trigger timing of a Contrast Enhanced Magnetic Resonance Angiography (CE-MRA) scan.

BACKGROUND

CE-MRA is a technique used in the field of MRI. In CE-MRA, a contrast agent (also referred to as angiography agent) is injected to a vessel to enhance the contrast of a nuclear magnetic resonance image to obtain a clear and visual image of the vessel.

Ideally, a CE-MRA scan is triggered (started) when the concentration of the contrast agent reaches a peak value in a Region of Interest (ROI). However, in fact, there is a time period from when the CE-MRA scan is triggered to when an image of the ROI is acquired by the CE-MRA scan.

In order to get an optimal trigger timing of the CE-MRA scan, a monitoring scan is performed to observe the flow of the contrast agent. As blood is flowing, a monitoring scan region (also called a monitor region) is generally arranged with an offset away from a CE-MRA scan region in the direction of the blood flow, as shown in FIG. 1. The monitor region is located in the same plane with the CE-MRA scan region so as to ensure that the monitor region is identical to the scan region or at least includes a part of the scan region. By arranging the monitor region to lead the scan region by the offset, an operator of a CE-MRA system is allowed to have enough time to trigger the CE-MRA scan when seeing the contrast agent in a fluoroscopic image (a monitor image) acquired from the monitoring scan.

U.S. Pat. No. 6,489,486B1 discloses a Magnetic Resonance (MR) pre-imaging method. In this U.S. patent application, a monitor region is located manually. In addition, the operator of an MR system must focus on the continuously-displayed fluoroscopic images so as to observe the flow of the contrast agent and determine a trigger timing for a CE-MRA scan. Therefore, the operator must be experienced.

Several methods have been developed in the prior art to trigger a CE-MRA scan automatically. U.S. Pat. No. 6,167,293A discloses a method for performing MRA. In this U.S. patent application, a signal value, i.e. the concentration of a contrast agent, in a pre-selected region, i.e. a monitor region, is monitored, and a CE-MRA scan is started automatically when the signal value exceeds a specified threshold value. In this method, the monitor region is also manually selected by an operator. Moreover, in this method, the advance or delay of the contrast agent peak due to the blood flow velocity is not taken into consideration.

BRIEF DESCRIPTION OF THE DRAWINGS

The present invention can be better understood by reference to the following description taken in conjunction with accompanying drawings. In the accompanying drawings, identical or like components are designated with identical or like reference signs designate. The accompanying drawings, together with the detailed description below, are incorporated into and form a part of the specification, and serve to further illustrate, by way of example, preferred embodiments of the present invention and to explain the principle and advantages of the present invention. In the accompanying drawings.

DETAILED DESCRIPTION

Figure 1:
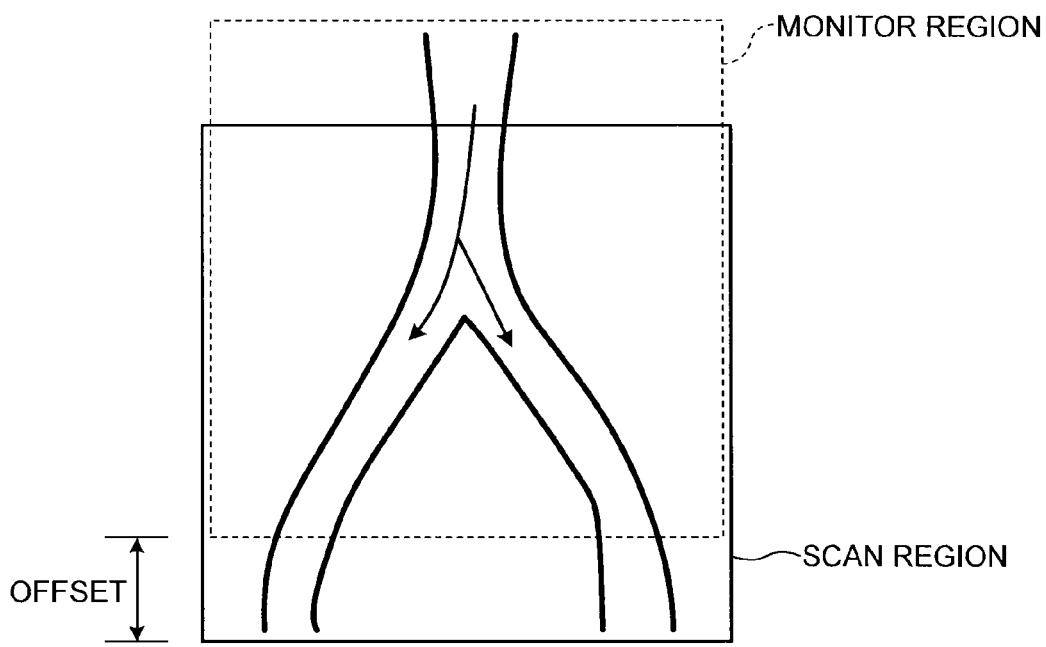
FIG. 1 is a schematic diagram illustrating a monitor region and a CE-MRA scan region.

The following presents a simplified summary of the present invention to provide a basic understanding of some aspects of the present invention. It should be understood that the summary is not an exhaustive summary of the present invention. It is not intended to identify the key or critical parts of the present invention, nor intended to limit the scope of the present invention. It only aims to present some concepts in a simplified form as a prelude to the more detailed description that is to be discussed later.

An object of the present invention is to provide an apparatus and a method for determining a trigger timing of a CE-MRA scan so as to automatically and accurately determine the trigger timing of the CE-MRA scan while take a blood flow velocity into consideration.

According to an aspect of the present invention, there is provided an apparatus for determining a trigger timing of a CE-MRA scan. The apparatus includes: a blood flow velocity acquisition unit configured to acquire a blood flow velocity of a target vessel; and a trigger timing determination unit configured to determine the trigger timing for performing the CE-MAR scan on a CE-MRA scan region according to the blood flow velocity and a predetermined image acquisition condition during a monitoring scan.

According to another aspect of the present invention, there is provided a method for determining a trigger timing of a CE-MRA scan. The method includes: acquiring a blood flow velocity of a target vessel; and determining the trigger timing for performing the CE-MAR scan on a CE-MRA scan region according to the blood flow velocity and a predetermined image acquisition condition during a monitoring scan.

Further, according to still another aspect of the present invention, there is provided a computer program for realizing the aforementioned method.

Additionally, according to still another aspect of the present invention, there is provided a computer program product, which is in the form of a medium at least readable to a computer, and on which computer program codes are recorded to realize the aforementioned method.

Embodiments of the present invention are described below with reference to the accompanying drawings. The elements and features described in a figure or an embodiment of the present invention can be combined with the elements and features shown in one or more other figures or embodiments. It should be noted that, for the purpose of clarity, representations and descriptions of elements and processes which are known to those skilled in the art or are not related to the present invention, are not presented in the drawings and the description.

The method for determining a trigger timing of a CE-MRA scan according to embodiments of the present invention is described below with reference to FIG. 2 to FIG. 10.

Figure 2:
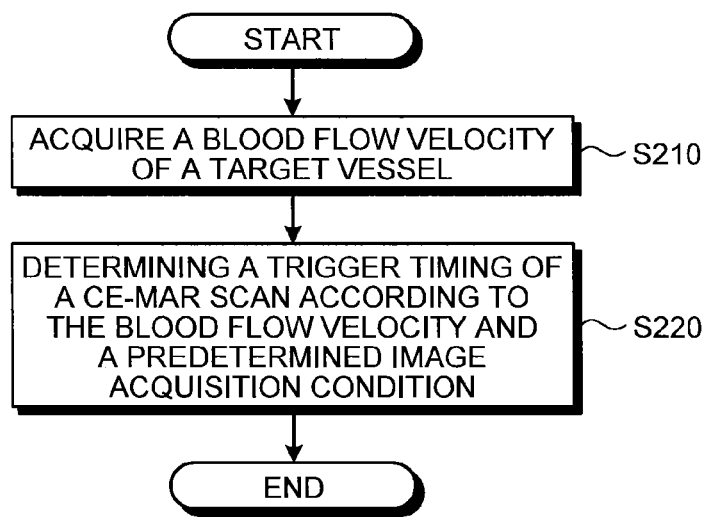
FIG. 2 is a schematic flow chart illustrating a method for determining a trigger timing of a CE-MRA scan according to an embodiment of the present invention.

FIG. 2 is a schematic flow chart illustrating a method for determining a trigger timing of a CE-MRA scan according to an embodiment of the present invention. In this method, a blood flow velocity of a target vessel is acquired in step S210.

A predetermined blood flow velocity may be used in the method according to the embodiment of the present invention. For example, a predetermined blood flow velocity that is received from outside may be used as the blood flow velocity of the target vessel. The predetermined blood flow velocity may be, for example, a previous measurement result of an individual to be scanned, or a statistical blood flow velocity of a group to which the individual to be scanned belongs.

An actual blood flow velocity of the target vessel may also be used in the method according to the embodiment of the present invention. As the blood flow velocities are different depending on the individuals to be scanned, the use of an actual blood flow velocity can allow the determined trigger timing more accurate.

In an embodiment of the present invention, a plurality of time-phase images are acquired through monitoring scans on a monitor region, and then are used to detect a blood flow velocity of the target vessel. The actual blood flow velocity can be detected using various appropriate methods existing in the prior art. As an example rather than a limitation, in an embodiment of the present invention, a target vessel may be detected in a plurality of time-phase images, and then, a blood flow velocity of the target vessel is calculated according to a difference of the lengths of the target vessel in any two of the plurality of time-phase images and the time interval between the two time-phase images. The blood flow velocity is equal to the difference of the lengths divided by the time interval. Certainly, the aforementioned method is only an example, and there may be other blood flow velocity calculation methods. For example, the blood flow velocity of the target vessel may be obtained by averaging the blood flow velocities calculated based on each two of the plurality of time-phase images. Such methods for calculating the blood flow velocity are not listed here one by one.

In a fluoroscopic image acquired by the monitoring scans, the part where the contrast agent locates generally has a higher brightness than the brightness of the other parts in the image. Therefore, the contrast agent flowing in the target vessel can be easily identified in the fluoroscopic image so as to identify the target vessel. The flow speed of the contrast agent represents the flow speed of the blood in the target vessel. The length of the detected target vessel can be represented by the length of the identified contrast agent.

Then, in step S220, a trigger timing for performing a CE-MAR scan on a CE-MRA scan region is determined during the monitoring scan period according to the blood flow velocity and a predetermined image acquisition condition. Specifically, a time that is needed from the triggering of a CE-MRA scan to the acquisition of an effective CE-MRA scan image is determined according to the image acquisition condition. If an effective CE-MRA scan image is acquired at the time point at which the concentration of the contrast agent reaches a peak value in the ROI (scan region), the triggering of the CE-MRA scan needs to be advanced the time (also referred to as a scan lead time) that is needed from the triggering of a CE-MRA scan to the acquisition of an effective CE-MRA scan image. The trigger timing of the CE-MRA scan is determined according to the blood flow velocity and the scan lead time.

In a CE-MRA system, the asynchrony of the time point when the CE-MRA scan is triggered and the time point when an effective CE-MRA scan image is acquired is closely related to the image acquisition condition. First, the scan sequences used for a monitoring scan and a CE-MRA scan are different, so it takes a time period (hereinafter referred to as a sequence switching time) to switch from the monitoring scan to the CE-MRA scan. In the same system, the sequence switching time is related to the type of the sequence used for a CE-MRA scan. Certainly, the sequence switching time may be different in different systems. Secondarily, a k-space filling method is generally used in a CE-MRA scan to form a CE-MRA image. In the k-space filling method, the CE-MRA image formed at the time when the center of the k-space is filled has the optimal quality. The time elapsed from the time point when a k-space filling is started to the time point when the center of the k-space is filled is called a k-space centric-filling time. The k-space centric-filling time is related to the type of the k-space filling method. For example, in a sequential k-space e filling method, the k-space centric-filling time is half of a complete k-space filling time TA, that is, TA/2. In a center-preferential k-space filling method, the k-space centric-filling time is zero. Therefore, preferably but not necessarily, the image acquisition condition of the type of a k-space e filling method may be taken into consideration so as to acquire a high-quality CE-MRA image.

Figure 3:
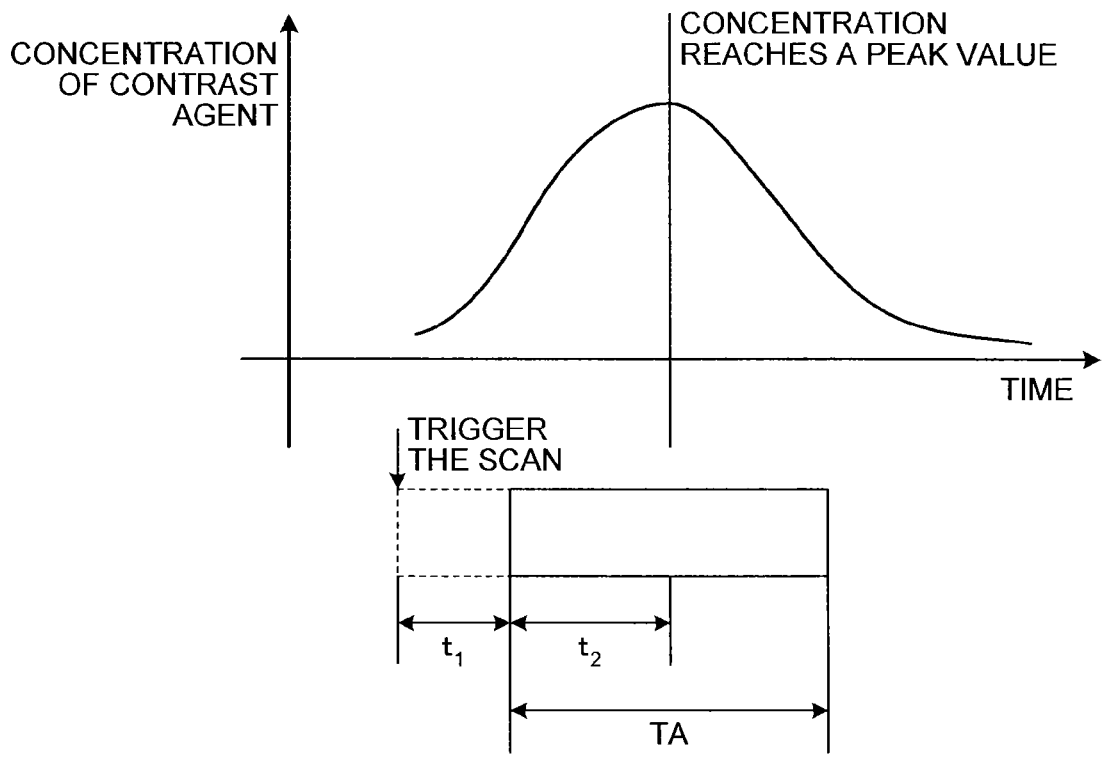
FIG. 3 is a schematic diagram illustrating a time period between the time point when a CE-MRA scan is triggered and the time point when an effective CE-MRA scan image is acquired.

In order to facilitate understanding, FIG. 3 shows a schematic diagram illustrating a time period between the time point when a CE-MRA scan is triggered and the time point when an effective CE-MRA scan image is acquired. Ideally, an effective CE-MRA scan image is acquired at the time point when the concentration of the contrast agent reaches a peak value. As shown in FIG. 3, a time period t1 and a time period t2 elapse from the time point when the scan is triggered to the time point when the concentration of the contrast agent reaches the peak value. Here, t1 represents a sequence switching time, and t2 represents a k-space centric-filling time. TA represents the time for a complete k-space filling. In the example shown in FIG. 3, the k-space centric-filling time is taken into consideration. The image scanned when the center of the k-space is filled has the optimal quality. However, it should be appreciated that the k-space centric-filling time may not be taken into consideration.

It can be seen from FIG. 3 that if the CE-MRA scan is triggered manually, the operator of the CE-MRA system needs to be skilled in determining the trigger timing according to various image acquisition conditions. In addition, as manual operations have a poor consistency and the determined trigger timing may be different at each time, the time between the time point when an effective CE-MRA scan image is acquired and the time point when the concentration of the contrast agent reaches the peak value may be different, resulting in a difference in contrasts of the CE-MRA scan images.

In view of this, in the method according to an embodiment of the present invention, a trigger timing for performing a CE-MAR scan on a CE-MRA scan region is determined according to a blood flow velocity and a predetermined image acquisition condition.

Figure 4:
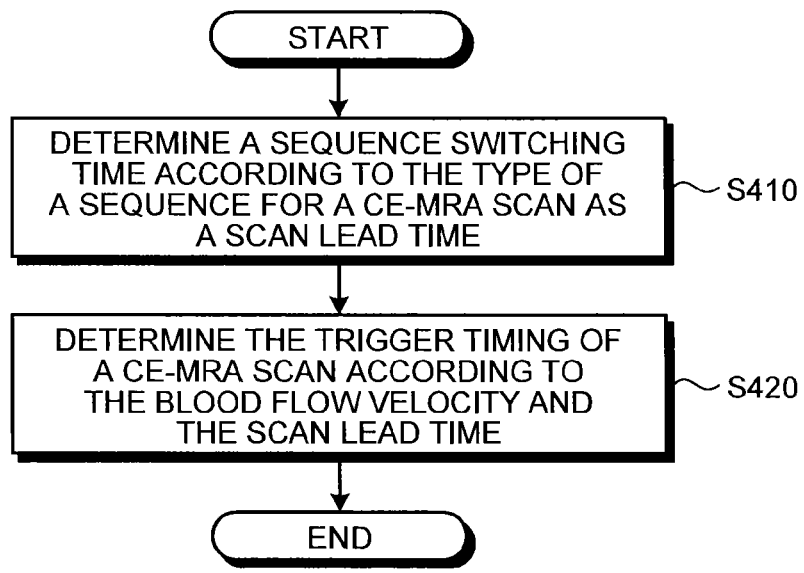
FIG. 4 is a schematic flow chart illustrating a step of determining a trigger timing according to an embodiment of the present invention.

FIG. 4 is a schematic flow chart illustrating a step of determining a trigger timing according to an embodiment of the present invention. In this embodiment, the image acquisition condition taken into consideration is the type of a sequence for the CE-MRA scan. As shown in FIG. 4, in step S410, a sequence switching time is determined as a scan lead time according to the sequence type for the CE-MRA scan. The sequence switching time is the time needed for switching from a monitoring scan to a CE-MRA scan of the sequence type. In step S420, the trigger timing is determined according to the blood flow velocity and the scan lead time. The details of the determining of the trigger timing according to the blood flow velocity and the scan lead time will be described later.

Figure 5:
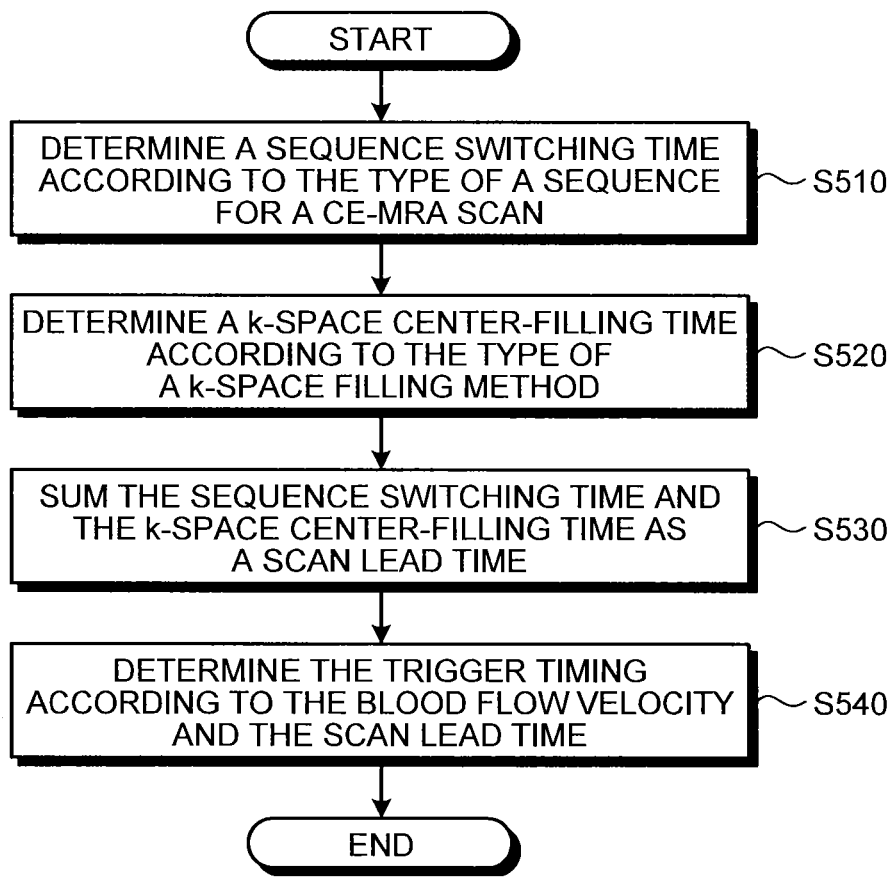
FIG. 5 is a schematic flow chart illustrating a step of determining a trigger timing according to another embodiment of the present invention.

FIG. 5 is a schematic flow chart illustrating a step of determining a trigger timing according to another embodiment of the present invention. In this embodiment, the following two image acquisition conditions are taken into consideration: the type of a sequence for the CE-MRA scan, and the type of a k-space filling method to be used in the CE-MRA scan. As shown in FIG. 5, in step S510, a sequence switching time is determined according to the type of the sequence for the CE-MRA scan. In step S520, a k-space centric-filling time is determined according to the type of the k-space filling method. In step S530, the sequence switching time and the k-space centric-filling time are summed as a scan lead time. Then, in step S540, the trigger timing of the CE-MRA scan is determined according to the blood flow velocity and the scan lead time.

It should be appreciated that in the case of the same sequence type of CE-MRA scan, different CE-MRA systems may have different sequence switching times. The sequence switching time and the type of a k-space filling method for a CE-MRA system are generally predetermined as parameters of the CE-MRA system, and can be acquired conveniently when it is needed to use these parameters. The k-space centric-filling time, which is corresponding to the type of the k-space filling method, can be calculated using any existing appropriate method.

After the trigger timing of the CE-MRA scan is determined, the CE-MRA scan can be triggered manually or automatically as needed. For example, the CE-MRA scan can be triggered manually by the operator though pressing a CE-MRA scan button, or be triggered automatically with a signal.

As examples, several embodiments of determining a trigger timing according to a blood flow velocity and a scan lead time are described below.

1. Position Triggering

According to an embodiment of the present invention, a trigger timing of a CE-MRA scan is determined according to the position of a contrast agent.

First, a scan lead distance is calculated according to a blood flow velocity and a scan lead time. The scan lead distance is a product of the blood flow velocity and the scan lead time. As stated above, the scan lead time is the time needed from the triggering of a CE-MRA scan to the acquisition of an effective CE-MRA scan image. Accordingly, the scan lead distance represents a distance that the blood flows through from the time point when the CE-MRA is triggered to the time point when an effective scanned CE-MRA is acquired.

Then, a trigger position is determined according to the scan lead distance and a CE-MRA scan region. Considering the scan lead distance, the trigger position is set at a position that a position for acquiring an effective CE-MRA scan image is to reach after being moved the scan lead distance in a direction reverse to the blood flow direction. In general, the position where an effective CE-MRA scan image is acquired is substantially overlapped with a downstream boundary of the CE-MRA scan region in the blood flow direction. That is, the image acquired by the CE-MRA scan is the image at the time point when the contrast agent arrives at the downstream boundary of the scan region. In this way, the acquired CE-MRA scan image can clearly present the whole outline of the target vessel in the ROI.

Figure 6:
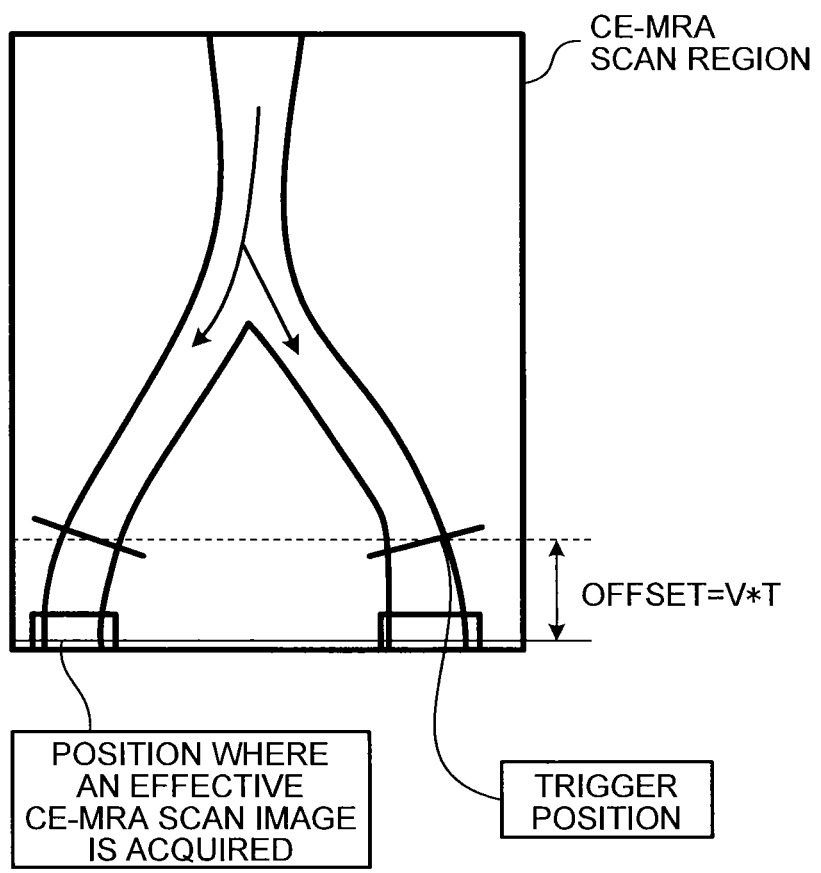
FIG. 6 is a schematic diagram illustrating a trigger position according to an embodiment of the present invention.

In order to facilitate understanding, FIG. 6 is a schematic diagram illustrating a trigger position according to an embodiment of the present invention. In FIG. 6, the reference sign "Offset" represents a scan lead distance, which is equal to a product of a blood flow velocity V and a scan lead time T. The solid line in the horizontal direction represents a position where an effective CE-MRA scan image is acquired. The dotted line in the horizontal direction represents a position where a CE-MRA scan is triggered.

A CE-MRA scan is triggered when it is detected through a monitoring scan that the contrast agent in the target vessel arrives at the trigger position.

In practical applications, in order to provide a manual triggering mechanism, the determined trigger position may be displayed on a fluoroscopic image acquired from the monitoring scan. The operator can trigger a CE-MRA scan manually when seeing that the contrast flows and arrives at the trigger position.

Additionally, in a variation of this embodiment, when the determined trigger position is outside the monitor region for a monitoring scan, the monitor region can be expanded automatically such that the trigger position is in the expanded monitor region. In this way, the method according to the embodiment becomes more robust. The monitor region can be expanded using various methods that are existing in the prior art or will be developed in future. These methods are not described in detail herein in order not to obscure the present invention.

2. Countdown Triggering

According to another embodiment of the present invention, a trigger timing of a CE-MRA scan is determined through countdown.

First, a residual trigger time is calculated according to a blood flow velocity, a CE-MRA region and a position at which a contrast agent in a target vessel currently arrives and which is detected through a monitoring scan. The residual trigger time is the time needed for the contrast agent to flow from the current position until the CE-MRA scan is triggered. Ideally, the residual trigger time is equal to a distance between the current position of the contrast agent in the target vessel and a downstream boundary (where an effective CE-MRA scan image is generally acquired) of the CE-MRA region in the blood flow direction divided by the blood flow velocity.

Considering the fact that there is a time period, i.e. a scan lead time, from the triggering to the acquisition of an effective CE-MRA scan image, the scan lead time is subtracted from the residual trigger time.

It is determined to trigger the CE-MRA scan when it is determined through countdown that the residual trigger time subtracted by the scan lead time has elapsed.

In practical applications, in order to provide a manual triggering mechanism, the residual trigger time may be displayed on a fluoroscopic image acquired from a monitoring scan in a countdown manner. The operator can trigger the CE-MRA scan manually when seeing that the residual trigger time is zero or approximates to zero.

The method in this embodiment has no limitation on the trigger position, and will not be influenced no matter the trigger position is in or outside the scan region.

3. Position and Countdown Combined Triggering

The time needed for a CE-MRA system to display a frame of image is referred to as a machine time. For a monitoring scan, the machine time is substantially equal to the inter-frame time interval of the monitoring scan. In the case of using position triggering, if the trigger timing is during a machine time, a CE-MRA scan may be triggered later. For example, the contrast agent may not arrive at the trigger position in a frame of image but exceed the trigger position in the next frame of image. Therefore, the triggering of the CE-MRA scan in the next frame of image is late, missing the time point at which the concentration of the contrast agent reaches the peak value.

In view of this, according to another embodiment of the present invention, a trigger timing of a CE-MRA scan is determined by combining the trigger position and the countdown. In the embodiment, a trigger timing is determined through the following steps of:

a) calculating a scan lead distance L according to a blood flow velocity and a scan lead time;

b) determining a trigger position P according to the scan lead distance and a CE-MRA scan region;

c) calculating, according to the blood flow velocity, a time $T_{tr}$ needed for a contrast agent in the target vessel to flow to the trigger position from the current position of the contrast agent detected through a monitoring scan, as a residual trigger time;

d) performing a modular operation on the residual trigger time $T_{tr}$ with an inter-frame time interval $T_{intv}$ of the monitoring scan as a modulus: $r=T_{tr} \% T_{intv}$, and assuming the quotient resulting from the modular operation is m;

e) if the remainder r resulting from the modular operation is not zero, starting to count down when m fluoroscopic images have been displayed, that is, when the number of the frames scanned through the monitoring scan is equal to the quotient m resulting from the modular operation, and determining triggering a CE-MRA scan when it is determined through the countdown that a time equal to the remainder r resulting from the modular operation has elapsed;

f) if the remainder r resulting from the modular operation is zero, determining triggering the CE-MRA scan when it is detected through the monitoring scan that the contrast agent in the target vessel arrives at the trigger position.

In the steps above, steps a), b) and c) can be exchanged in execution order without limitation.

By using the method provided in this embodiment, a trigger timing can be determined accurately in the case that the trigger timing is during a machine time.

4. Frame Number and Countdown Combined Triggering

As an alternative of the above embodiment in which the position and the countdown are combined to determine a trigger timing, in another embodiment of the present invention, a trigger timing of a CE-MRA scan is determined by combining a frame number and the countdown.

In this embodiment, the step of determining a trigger timing includes the following steps of:

a) calculating, according to the blood flow velocity, a time $T_{tr}$ needed for a contrast agent in the target vessel to flow to the trigger position from the current position of the contrast agent detected through a monitoring scan as a residual trigger time;

b) performing a modular operation on the residual trigger time $T_{tr}$ with an inter-frame time interval $T_{intv}$ of the monitoring scan as a modulus: $r=T_{tr} \% T_{intv}$ and assuming the quotient resulting from the modular operation is m;

c) if the remainder r resulting from the modular operation is not zero, starting to count down when m fluoroscopic images have been displayed, that is, when the number of the frames scanned through the monitoring scan is equal to the quotient m resulting from the modular operation, and determining triggering a CE-MRA scan when it is determined through the countdown that a time equal to the remainder r resulting from the modular operation has elapsed;

d) if the remainder r resulting from the modular operation is zero, determining triggering a CE-MRA scan when m fluoroscopic images are displayed, that is, when the number of the frames scanned through the monitoring scan is equal to the quotient m resulting from the modular operation.

By using the method provided in this embodiment, a trigger timing can be determined accurately in the case that the trigger timing is during a machine time.

Compared with the steps in the above embodiment in which a trigger timing is determined by combining a position and the countdown, it is not necessary to calculate the trigger position in this embodiment.

In a variation of the embodiment of the present invention, the CE-MAR scan is started when the residual trigger time $T_{tr}$ elapses in the case that the $T_{tr}$ is shorter than the inter-frame time interval $T_{intv}$. The residual trigger time $T_{tr}$ is calculated and corrected frame by frame.

Under the guide of the above description, those skilled in the art can implement the determining of the trigger timing according to a blood flow velocity and a scan lead time in various ways, which will not be listed herein.

In addition, in the above embodiments, the trigger timing can be corrected in real time, if needed. For example, the trigger position or the residual trigger time can be corrected in real time according to the blood flow velocity detected in real time during the monitoring scan.

One or more target vessels may be detected in the monitor region. For example, two great vessels may be detected when the monitor region is at the lower limbs of a human body. For another instance, when the monitor region is at a pelvis, the target vessel is a tree-shaped vessel with a plurality of branches, and the number of target vessels is equal to that of the branches. The blood flow velocities of the plurality of target vessels may be different. According to an embodiment of the present invention, in the case that a plurality of target vessels are detected, the smallest one of the blood flow velocities of the plurality of target vessels is used to determine the trigger timing. This can guarantee that the contrast agent arrives at all the target vessels when an effective CE-MRA scan image is acquired.

In order to facilitate understanding, an example of a monitor region containing a plurality of target vessels is given below. This example is merely illustrative of the present invention, but is construed as limiting the number of target vessels.

Figure 7A:
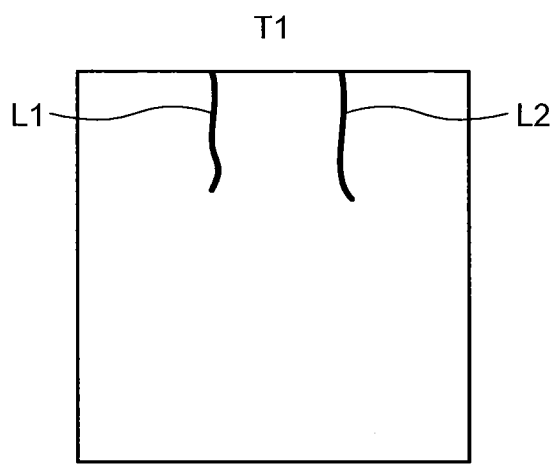
FIG. 7a-FIG. 7b are schematic diagrams showing a monitor region containing two target vessels.
Figure 7B:
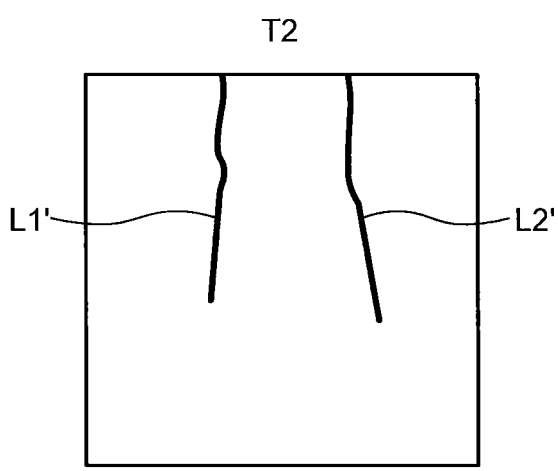

FIG. 7a-FIG. 7b are schematic diagrams showing a monitor region containing two target vessels. In this example, the lengths of the two target vessels are respectively L1 and L2 at a time point T1 and L1' and L2' at a time point T2. Then, the blood flow velocity of the left target vessel is calculated as $$V1 = \frac{L1' - L1}{T2 - T1},$$

and the blood flow velocity of the right target vessel is calculated as $$V2 = \frac{L2' - L2}{T2 - T1}.$$

The smallest one of the V1 and the V2 (min(V1,V2)) is used as a blood flow velocity for determining the trigger timing.

Figure 8A:
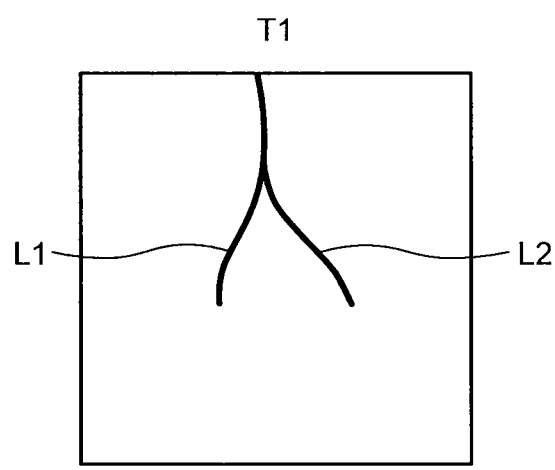
FIG. 8a-FIG. 8b are schematic diagrams showing a monitor region containing tree-shaped target vessels.
Figure 8B:
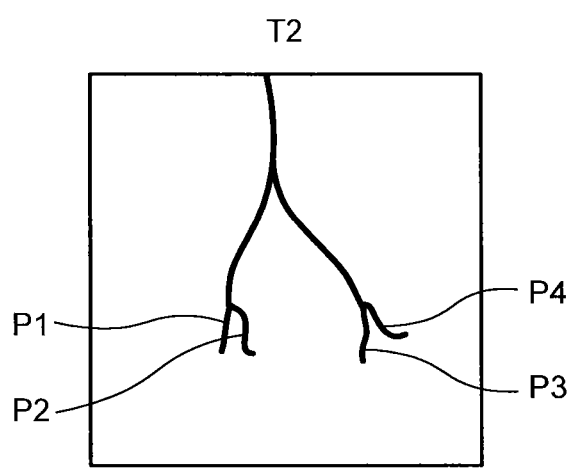

FIG. 8a-FIG. 8b are schematic diagrams showing a monitor region containing tree-shaped target vessels. In this example, a target vessel has two branches, the lengths of which are L1 and L2 respectively, at a time point T1, and has four branches, the lengths of which are P1, P2, P3 and P4 respectively, at a time point T2. That is, there are four target vessels in the monitor region. Accordingly, the blood flow velocities of the four branches are respectively calculated according to the following formulas:

$$V1 = \frac{P1 - L1}{T2 - T1}, V2 = \frac{P2 - L1}{T2 - T1}, V3 = \frac{P3 - L2}{T2 - T1} \text{ and } V4 = \frac{P4 - L2}{T2 - T1}.$$

The smallest one of the four velocities (min(V1,V2,V3,V4)) is used as a blood flow velocity for determining the trigger timing.

In the method for determining a trigger timing of a CE-MRA scan according to embodiments of the present invention, the monitor region can be manually set as in the prior art. In order to set the monitor region more accurately, according to an embodiment of the present invention, the monitor region for a monitoring scan may be determined according to the predetermined blood flow velocity of the target vessel, the predetermined image acquisition condition and the CE-MRA scan region before starting the monitoring scan.

In the prior art, in order to facilitate the operation of the operator, a monitor region is generally set in such a way that a CE-MRA scan is triggered when the contrast agent flows to a downstream boundary of the monitor region in the blood flow direction. Therefore, in the embodiment of the present invention, the downstream boundary of the monitor region may also be set to substantially correspond to the trigger position, while there is no limitation to the upstream boundary of the monitor region in the blood flow direction. Certainly, the present invention is not limited to this case, and the downstream boundary of the monitor region can also be located downstream from the trigger position. In addition, in the case that the CE-MRA scan is triggered through countdown rather than though determining the position of the contrast agent, as described in some above-described embodiments, the downstream boundary of the monitor region may also be located upstream from an actual trigger position.

Figure 9:
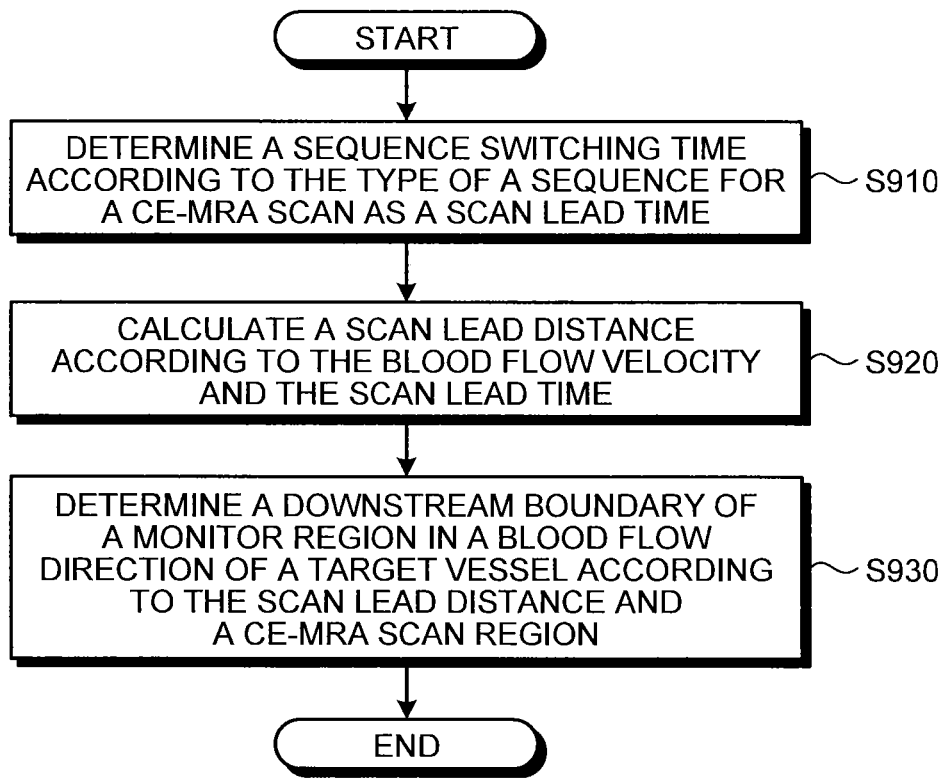
FIG. 9 is a schematic flow chart illustrating a step of determining a monitor region according to an embodiment of the present invention.

As a specific example, FIG. 9 shows a schematic flow chart illustrating a step of determining a monitor region according to an embodiment of the present invention. In this embodiment, the image acquisition condition includes the type of a sequence for the CE-MRA scan. As shown in FIG. 9, in step S910, a sequence switching time is determined according to the type of the sequence for the CE-MRA scan as a scan lead time. In step S920, a scan lead distance is calculated according to a blood flow velocity and the scan lead time. In step S930, a downstream boundary of the monitor region in a blood flow direction of the target vessel is determined according to the scan lead distance and a CE-MRA scan region. Specifically, the downstream boundary of the monitor region is set at a position that the downstream boundary of the CE-MRA scan region in the blood flow direction is to reach after being moved the scan lead distance in a direction inverse to the blood flow direction.

Figure 10:
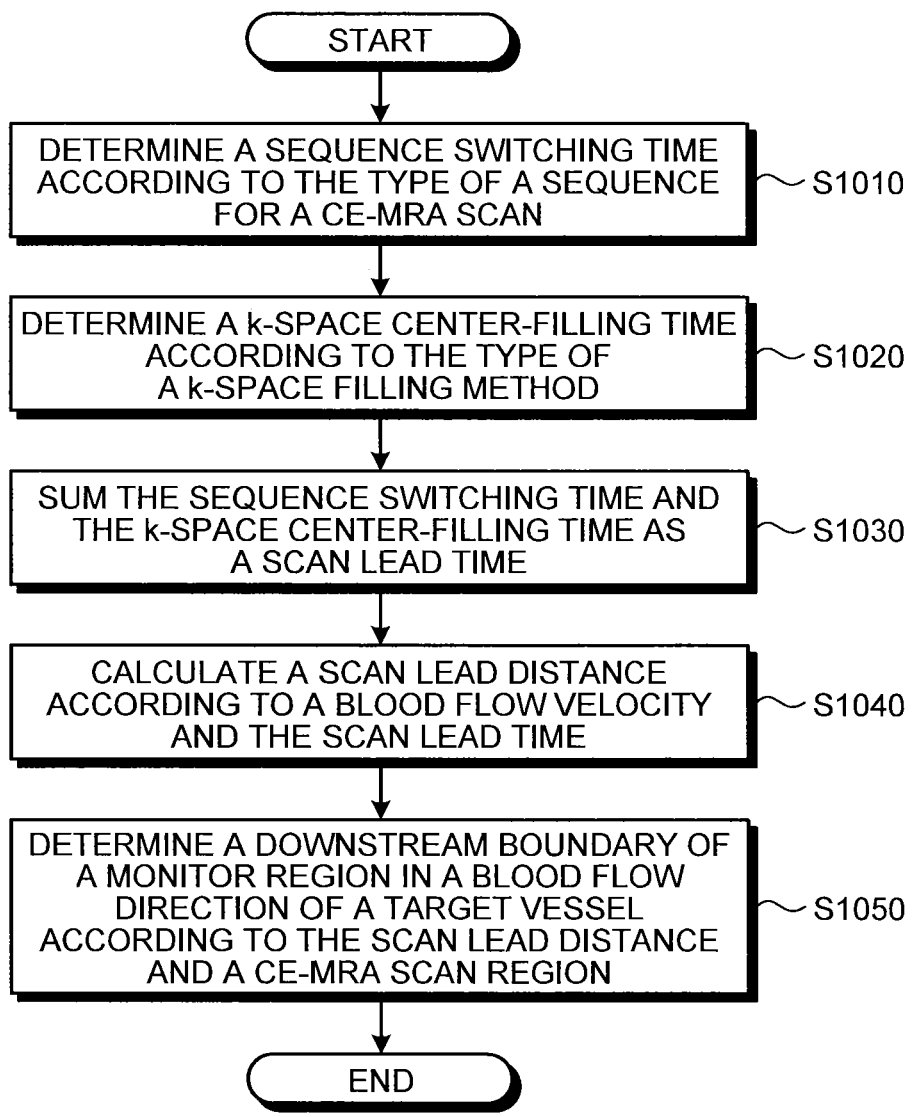
FIG. 10 is a schematic flow chart illustrating a step of determining a monitor region according to another embodiment of the present invention.

FIG. 10 is a schematic flow chart illustrating a step of determining a monitor region according to another embodiment of the present invention. In this embodiment, the image acquisition condition includes the type of the sequence for the CE-MRA scan and the type of the k-space filling method to be used in the CE-MRA scan. As shown in FIG. 10, in step S1010, a sequence switching time is determined according to the type of the sequence for the CE-MRA scan as a scan lead time. In step S1020, a k-space centric-filling time is determined according to the type of the k-space filling method. In step S1030, the sequence switching time and the k-space centric-filling time are summed as a scan lead time. In step S1040, a scan lead distance is calculated according to a blood flow velocity and the scan lead time. In step S1050, a downstream boundary of the monitor region in a blood flow direction of the target vessel is determined according to the scan lead distance and the CE-MRA scan region. Specifically, similar to the embodiment shown in FIG. 9, the downstream boundary of the monitor region is set at a position that the downstream boundary of the CE-MRA scan region in the blood flow direction is to reach after being moved the scan lead distance in a direction inverse to the blood flow direction.

In the embodiments shown in FIG. 9 and FIG. 10, the monitor region and the CE-MRA scan region are set in the same plane as in the prior art.

An apparatus for determining a trigger timing of a CE-MRA scan according to embodiments of the present invention is described below with reference to FIG. 11-FIG. 21.

Figure 11:
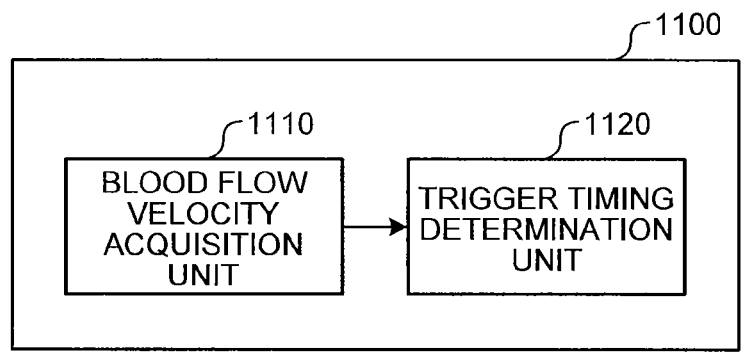
FIG. 11 is a schematic block diagram illustrating an apparatus for determining a trigger timing of a CE-MRA scan according to an embodiment of the present invention.

FIG. 11 is a schematic block diagram illustrating an apparatus for determining a trigger timing of a CE-MRA scan according to an embodiment of the present invention. As shown in FIG. 11, an apparatus 1100 for determining a trigger timing of a CE-MRA scan includes a blood flow velocity acquisition unit 1110 and a trigger timing determination unit 1120. The blood flow velocity acquisition unit 1110 is configured to acquire a blood flow velocity of a target vessel.

A predetermined blood flow velocity may be used in the apparatus according to an embodiment of the present invention. According to an embodiment of the present invention, the blood flow velocity acquisition unit 1110 is further configured to receive from outside a predetermined blood flow velocity as the blood flow velocity of the target vessel.

Figure 12:
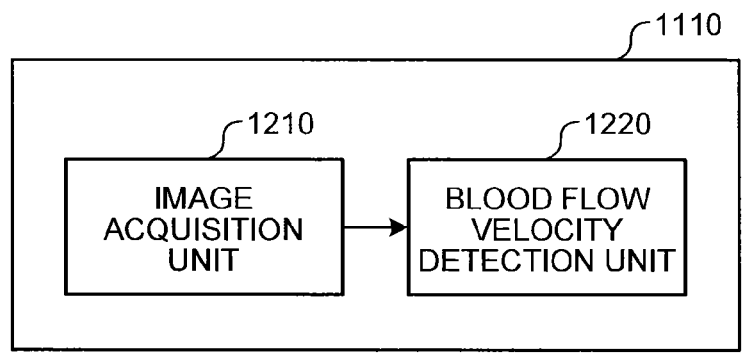
FIG. 12 is a schematic block diagram illustrating a blood flow velocity acquisition unit according to an embodiment of the present invention.

An actual blood flow velocity of the target vessel may also be used in the apparatus according to an embodiment of the present invention. FIG. 12 is a schematic block diagram illustrating a blood flow velocity acquisition unit according to an embodiment of the present invention. In this embodiment, the blood flow velocity acquisition unit 1110 may include an image acquisition unit 1210 and a blood flow velocity detection unit 1220. The image acquisition unit 1210 is configured to acquire a plurality of time-phase images obtained by a monitoring scan on a monitor region. The blood flow velocity detection unit 1220 is configured to detect the blood flow velocity of the target vessel using the plurality of time-phase images.

The blood flow velocity detection unit 1220 may detect an actual blood flow velocity using various appropriate methods available in the prior art. As an example rather than a limitation, according to an embodiment of the present invention, the blood flow velocity detection unit 1220 includes a vessel detection unit and a blood flow velocity calculator (not shown). The vessel detection unit is configured to detect a target vessel in the plurality of time-phase images. The blood flow velocity calculator is configured to calculate the blood flow velocity of the target vessel according to a difference of the lengths of the target vessel in any two of the plurality of time-phase images and a time interval between the two time-phase images. The blood flow velocity is equal to the difference of the lengths divided by the time interval. Certainly, the aforementioned method is only an example, and there may be other blood flow velocity calculation methods. For example, the blood flow velocity of the target vessel may be obtained by averaging the blood flow velocities calculated based on each two of the plurality of time-phase images.

Further, according to another embodiment of the present invention, in the case that a plurality of target vessels are detected by the blood flow velocity detection unit 1220, the blood flow velocity detection unit uses the smallest one of the blood flow velocities of the plurality of target vessels calculated by the blood flow velocity calculator as a blood flow velocity for determining the trigger timing. This can guarantee that the contrast agent arrives at all the target vessels when an effective CE-MRA scan image is acquired.

In FIG. 11, the trigger timing determination unit 1120 is configured to determine the trigger timing for performing the CE-MAR scan on a CE-MRA scan region according to the blood flow velocity and a predetermined image acquisition condition during a monitoring scan. Specifically, the trigger timing determination unit 1120 may determine, according to the image acquisition condition, a time needed from the triggering of the CE-MRA scan to the acquisition of an effective CE-MRA scan image, i.e. a scan lead time. Then the trigger timing determination unit 1120 determines the trigger timing of the CE-MRA scan according to the blood flow velocity and the scan lead time.

Figure 13:
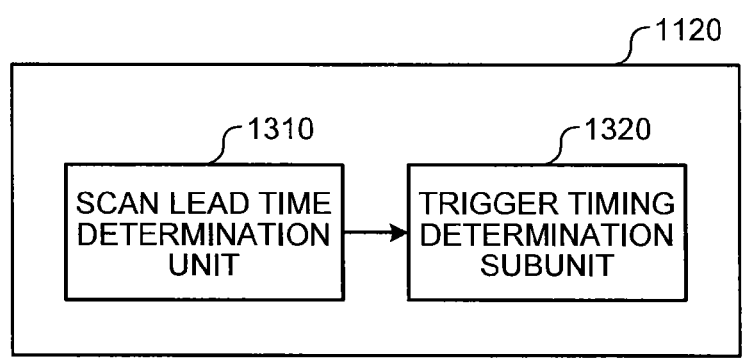
FIG. 13 is a schematic block diagram illustrating a trigger timing determination unit according to an embodiment of the present invention.

FIG. 13 is a schematic block diagram illustrating a trigger timing determination unit according to an embodiment of the present invention. In the embodiment shown in FIG. 13, the image acquisition condition includes the type of a sequence for the CE-MRA scan. As shown in FIG. 13, the trigger timing determination unit 1120 includes a scan lead time determination unit 1310 and a trigger timing determination subunit 1320. The scan lead time determination unit 1310 is configured to determine a sequence switching time according to the type of the sequence used for the CE-MRA scan as a scan lead time. The trigger timing determination subunit 1320 is configured to determine the trigger timing according to the blood flow velocity and the scan lead time.

Figure 14:
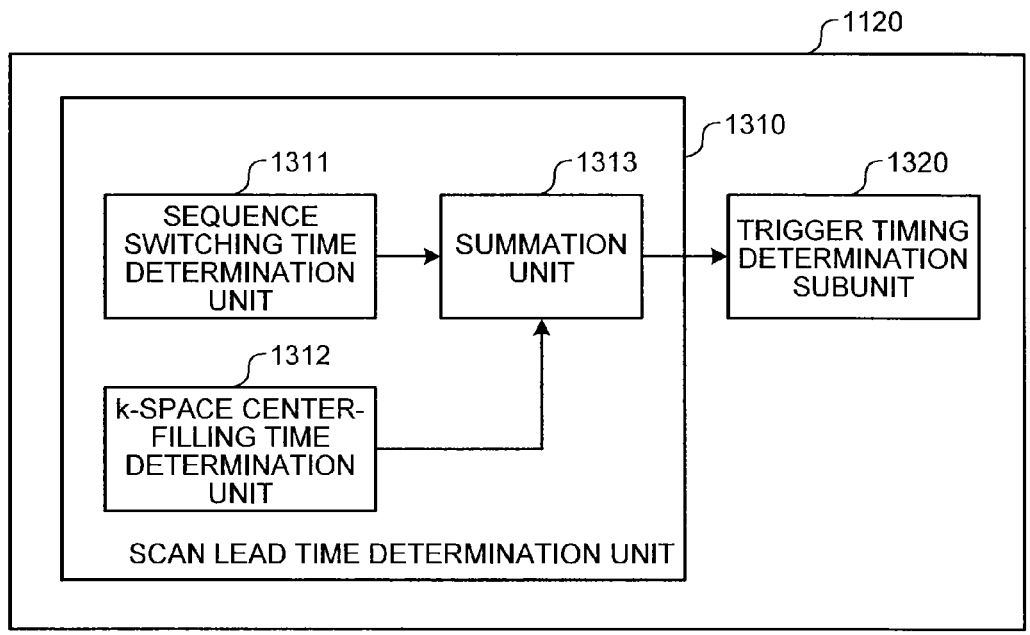
FIG. 14 is a schematic block diagram illustrating a trigger timing determination unit according to another embodiment of the present invention.

FIG. 14 is a schematic block diagram illustrating a trigger timing determination unit according to another embodiment of the present invention. In FIG. 14, the image acquisition condition includes the type of a sequence for the CE-MRA scan and the type of a k-space filling method to be used in the CE-MRA scan. The trigger timing determination unit 1120 includes a scan lead time determination unit 1310 and a trigger timing determination subunit 1320. The scan lead time determination unit 1310 is configured to determine a scan lead time, ad includes a sequence switching time determination unit 1311, a k-space centric-filling time determination unit 1312 and a summation unit 1313. The sequence switching time determination unit 1311 is configured to determine a sequence switching time according to the type of a sequence to be used in the CE-MRA scan. The k-space centric-filling time determination unit 1312 is configured to determine a k-space centric-filling time according to the type of a k-space filling method. The summation unit 1313 is configured to sum the sequence switching time and the k-space centric-filling time as the scan lead time. The trigger timing determination subunit 1320 is configured to determine the trigger timing according to the blood flow velocity and the scan lead time. In this embodiment, the k-space centric-filling time is included in the scan lead time so that a CE-MRA image of a better quality can be acquired.

After the trigger timing of the scan is determined, the CE-MRA scan can be triggered manually, or be triggered automatically by the trigger timing determination unit 1120, depending on the requirement. For example, the CE-MRA scan can be triggered by the operator through pressing a CE-MRA scan button, or be triggered automatically by the trigger timing determination unit 1120 via a signal.

Several specific embodiments of the trigger timing determination subunit are described below as examples.

Figure 15:
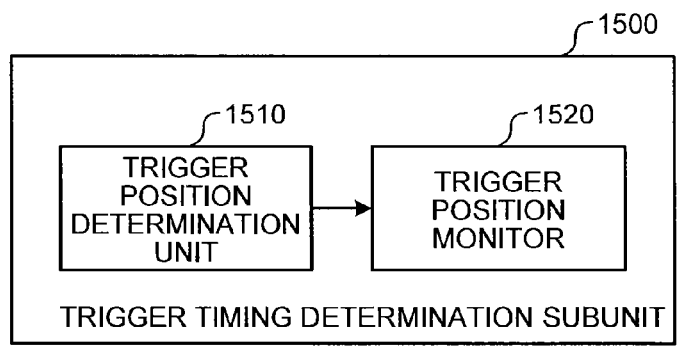
FIG. 15 is a schematic block diagram illustrating a trigger timing determination subunit according to an embodiment of the present invention.

FIG. 15 is a schematic block diagram illustrating a trigger timing determination subunit according to an embodiment of the present invention. In this embodiment, a trigger timing determination subunit 1500 determines the trigger timing based on a position. As shown in FIG. 15, the trigger timing determination subunit 1500 includes a trigger position determination unit 1510 and a trigger position monitor 1520. The trigger position determination unit 1510 is configured to calculate a scan lead distance according to the blood flow velocity and the scan lead time, and determine a trigger position according to the scan lead distance and the CE-MRA scan region. The scan lead distance is a product of the blood flow velocity and the scan lead time. The trigger position may be set at a position that a position for acquiring an effective CE-MRA scan image is to reach after being moved the scan lead distance in a direction reverse to the blood flow direction. The trigger position monitor 1520 is configured to determining triggering the CE-MRA scan when it is detected by the monitoring scan that the contrast agent in the target vessel arrives at the trigger position.

In a variation of this embodiment, the apparatus for determining a trigger timing of a CE-MRA scan may further include a monitor region adjustment unit (not shown). The monitor region adjustment unit is configured to expand a monitor region for a monitoring scan automatically when the trigger position determined by the trigging position determination unit 1510 is outside the monitor region, such that the trigger position is in the expanded monitor region.

Figure 16:
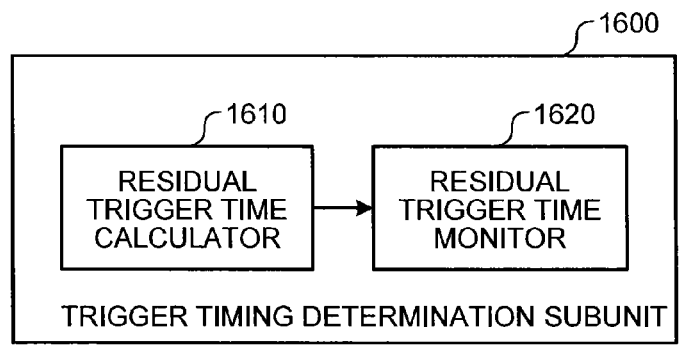
FIG. 16 is a schematic block diagram illustrating a trigger timing determination subunit according to another embodiment of the present invention.

FIG. 16 is a schematic block diagram illustrating a trigger timing determination subunit according to another embodiment of the present invention. In this embodiment, a trigger timing determination subunit 1600 determines the trigger timing through countdown. As shown in FIG. 16, the trigger timing determination subunit 1600 includes a residual trigger time calculator 1610 and a residual trigger time monitor 1620. The residual trigger time calculator 1610 is configured to calculate a residual trigger time according to the blood flow velocity, the CE-MRA scan region and a position at which a contrast agent in the target vessel currently arrives and which is detected through a monitoring scan, and subtract the scan lead time from the residual trigger time. The residual trigger time monitor 1620 is configured to determine triggering the CE-MAR scan when it is determined through countdown that the residual trigger time has elapsed. In this embodiment, whether or not the trigger position is in the monitor region does not influence the trigger timing determination subunit.

Figure 17:
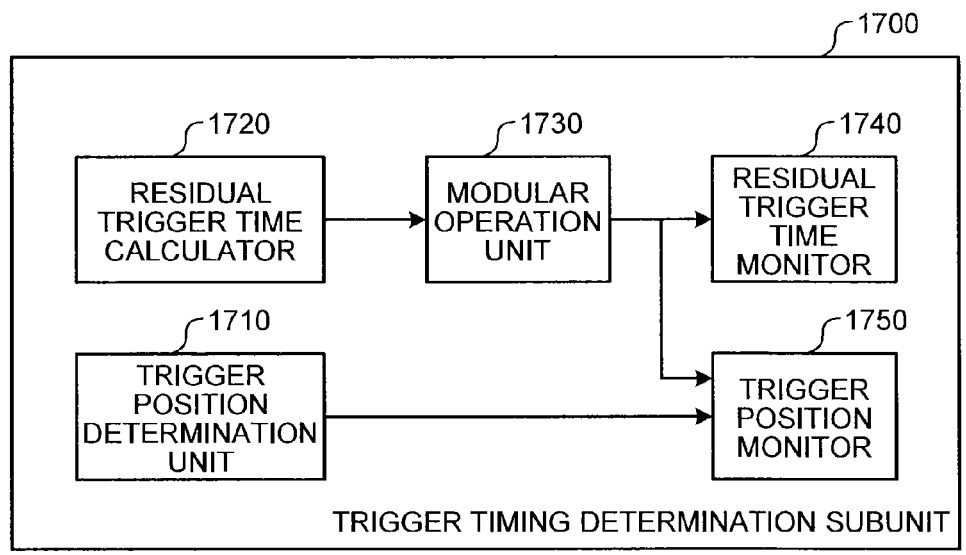
FIG. 17 is a schematic block diagram illustrating a trigger timing determination subunit according to another embodiment of the present invention.

FIG. 17 is a schematic block diagram illustrating a trigger timing determination subunit according to another embodiment of the present invention. In this embodiment, a trigger timing determination subunit 1700 determines the trigger timing based on a position and countdown. As shown in FIG. 17, the trigger timing determination subunit 1700 includes a trigger position determination unit 1710, a residual trigger time calculator 1720, a modular operation unit 1730, a residual trigger time monitor 1740 and a trigger position monitor 1750. The trigger position determination unit 1710 is configured to calculate a scan lead distance according to the blood flow velocity and the scan lead time, and determine a trigger position according to the scan lead distance and a CE-MRA scan region. The residual trigger time calculator 1720 is configured to calculate, according to the blood flow velocity, a time needed for the contrast agent in the target vessel to flow to the trigger position from a current position of the contrast agent detected through the monitoring scan, as the residual trigger time. The modular operation unit 1730 is configured to perform a modular operation on the residual trigger time with an inter-frame time interval of the monitoring scan as a modulus. The modular operation unit 1730 activates the residual time monitor 1740 if the remainder resulting from the modular operation is not zero. The modular operation unit 1730 activates the trigger position monitor 1750 if the remainder resulting from the modular operation is zero. The residual trigger time monitor 1740 is configured to start to count down when the same number of frames as a quotient resulting from the modular operation have been scanned through the monitoring scan. When it is determined through the countdown that a time equal to a remainder resulting from the modular operation has elapsed, the residual trigger time monitor 1740 determines triggering the CE-MRA scan. The trigger position monitor 1750 is configured to determine triggering the CE-MRA scan when it is detected through the monitoring scan that the contrast agent in the target vessel arrives at the trigger position. Through the trigger timing determination subunit according to this embodiment, the trigger timing can be determined accurately in the case that the trigger timing is during a machine time.

Figure 18:
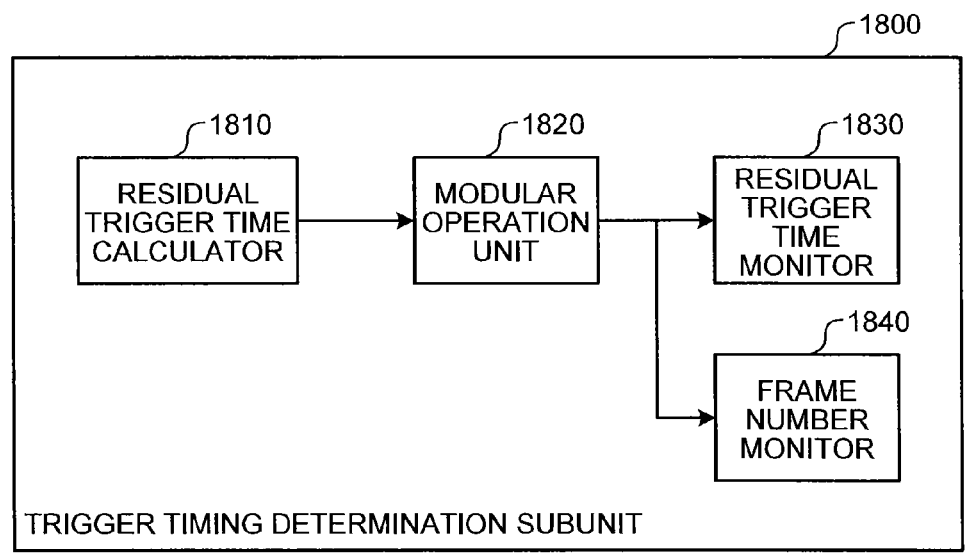
FIG. 18 is a schematic block diagram illustrating a trigger timing determination subunit according to another embodiment of the present invention.

FIG. 18 is a schematic block diagram illustrating a trigger timing determination subunit according to another embodiment of the present invention. In this embodiment, a trigger timing determination subunit 1800 determines the trigger timing based on a combination of a frame number and countdown. As shown in FIG. 18, the trigger timing determination subunit 1800 includes a residual trigger time calculator 1810, a modular operation unit 1820, a residual time monitor 1830 and a frame number monitor 1840. The residual trigger time calculator 1810 is configured to calculate, according to the blood flow velocity, a time needed for the contrast agent in the target vessel to flow to the trigger position from a current position of the contrast agent detected through a monitoring scan, as the residual trigger time. The modular operation unit 1820 is configured to perform a modular operation on the residual trigger time with an inter-frame time interval of the monitoring scan as a modulus. The modular operation unit 1820 activates the residual time monitor 1830 if a remainder resulting from the modular operation is not zero. The modular operation unit 1820 activates the frame number monitor 1840 if a remainder resulting from the modular operation is zero. The residual trigger time monitor 1830 is configured to start to count down when the same number of frames as a quotient resulting from the modular operation have been scanned through the monitoring scan. The residual trigger time monitor 1830 triggers the CE-MRA scan when it is determined though the countdown that a time equal to the remainder resulting from the modular operation has elapsed. The frame number monitor 1840 is configured to trigger the CE-MRA scan when the same number of frames as a quotient resulting from the modular operation have been scanned through the monitoring scan. Through the trigger timing determination subunit provided in this embodiment, a trigger timing can be determined accurately in the case that the trigger timing is during a machine time. Compared with the trigger timing determination subunit shown in FIG. 18, the trigger timing determination subunit provided in this embodiment needs not to calculate a trigger position.

Under the guide of the above description, those skilled in the art can implement the trigger timing determination subunit in various ways, which will not be listed herein.

In addition, in the above embodiments, the trigger timing determination unit 1120 may further configured to correct the trigger timing in real time as required. For example, the trigger position or the residual trigger time can be corrected in real time according to the blood flow velocity detected in real time during the monitoring scan.

The apparatus for determining a trigger timing of a CE-MRA scan according to an embodiment may further include a monitor region determination unit. The monitor region determination unit is configured to determine a monitor region for a monitoring scan automatically before the monitoring scan is started.

Figure 19:
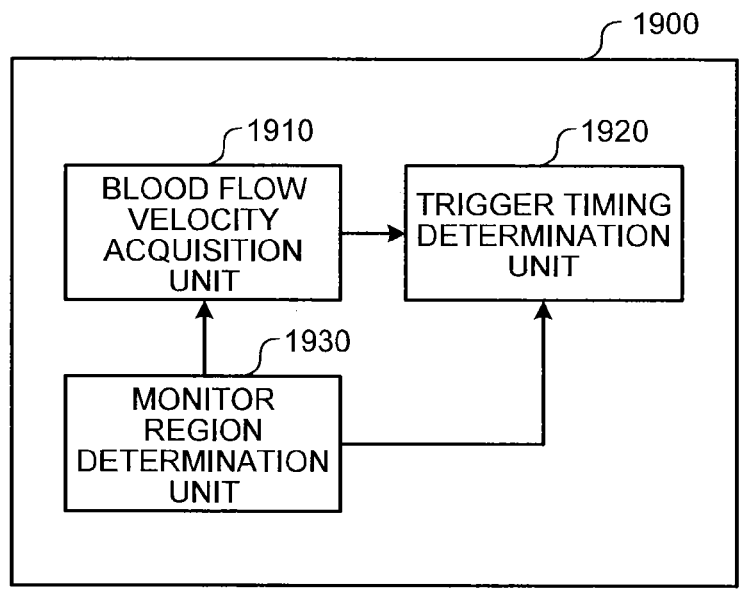
FIG. 19 is a schematic block diagram illustrating an apparatus for determining a trigger timing of a CE-MRA scan according to another embodiment of the present invention.

FIG. 19 is a schematic block diagram illustrating an apparatus for determining a trigger timing of a CE-MRA scan according to another embodiment of the present invention. Compared with the apparatus shown in FIG. 11, the apparatus 1900 shown in FIG. 19 is additionally provided with a monitor region determination unit 1930. The monitor region determination unit 1930 is configured to determine, before the monitoring scan is started, a monitor region for the monitoring scan according to the predetermined blood flow velocity of the target vessel, the predetermined image acquisition condition and a CE-MRA scan region. The blood flow velocity acquisition unit 1910 has substantially the same function with the blood flow velocity acquisition unit 1110 of the apparatus 1100 shown in FIG. 11. The trigger timing determination unit 1920 has substantially the same function with the trigger timing determination unit 1120 of the apparatus 1110 shown in FIG. 11. The monitor region determination unit 1930 can receive a predetermined blood flow velocity from outside, or acquire a predetermined blood flow velocity using the blood flow velocity acquisition unit 1910.

The downstream boundary of the monitor region in the blood flow direction can be set at substantially the same position as the trigger position. Therefore, the monitor region determination unit 1930 can determine the downstream boundary of the monitor region using the method used by the trigger position determination unit. There is no limitation to the upstream boundary of the monitor region in the blood flow direction. Further, as stated above, the downstream boundary of the monitor region may also be located at a position different from the trigger position.

Figure 20:
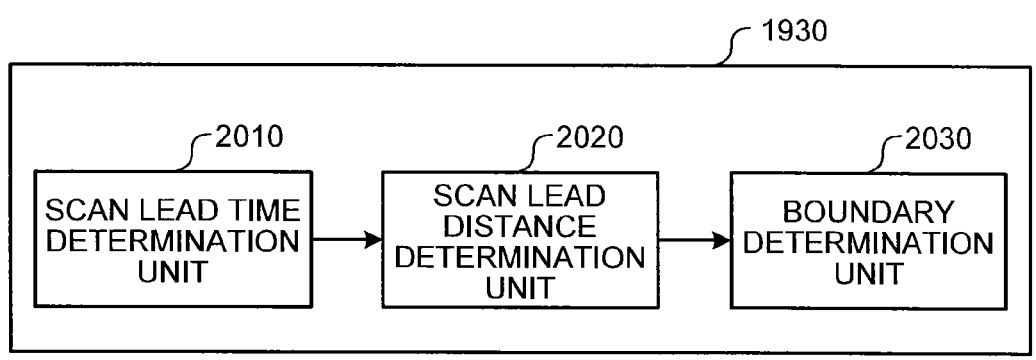
FIG. 20 is a schematic block diagram illustrating a monitor region determination unit according to an embodiment of the present invention.

FIG. 20 is a schematic block diagram illustrating a monitor region determination unit according to an embodiment of the present invention. In this embodiment, the image acquisition condition includes the type of a sequence for the CE-MRA scan. As shown in FIG. 20, the monitor region determination unit 1930 includes a scan lead time determination unit 2010, a scan lead distance determination unit 2020 and a boundary determination unit 2030. The scan lead time determination unit 2010 is configured to determine a sequence switching time according to the type of a sequence for the CE-MRA scan, as a scan lead time. The scan lead distance determination unit 2020 is configured to calculate a scan lead distance according to the blood flow velocity and the scan lead time. The boundary determination unit 2030 is configured to determine a downstream boundary of the monitor region in a blood flow direction of the target vessel according to the scan lead distance and the CE-MRA scan region. Specifically, the downstream boundary of the monitor region is set at a position that the downstream boundary of the CE-MRA scan region in the blood flow direction is to reach after being moved the scan lead distance in a direction inverse to the blood flow direction.

Figure 21:
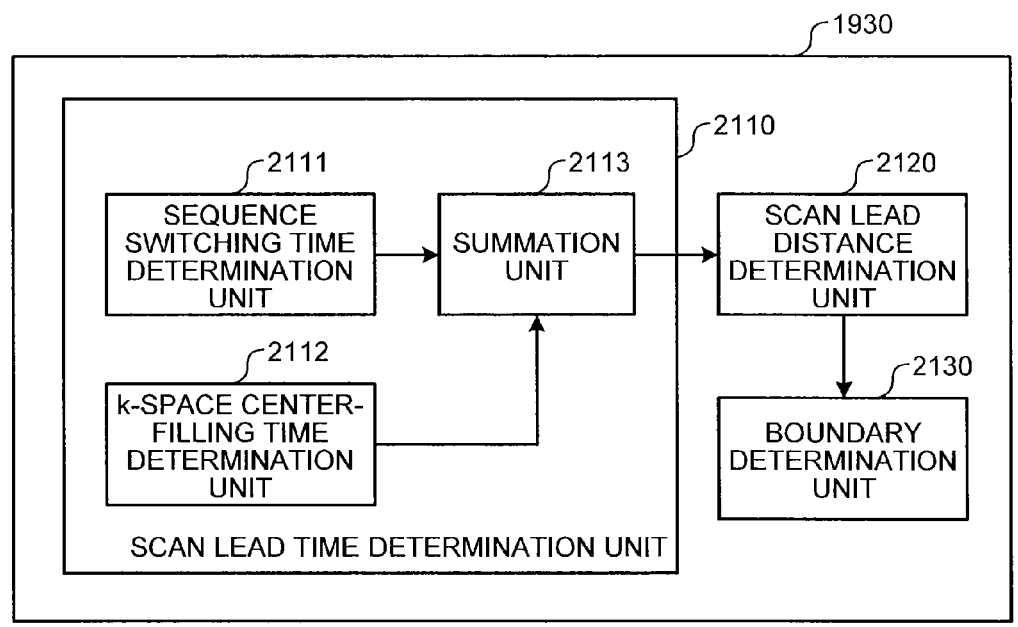
FIG. 21 is a schematic block diagram illustrating a monitor region determination unit according to another embodiment of the present invention.

FIG. 21 is a schematic block diagram illustrating a monitor region determination unit according to another embodiment of the present invention. In this embodiment, the image acquisition condition includes the type of a sequence for the CE-MRA scan and the type of a k-space filling method to be used in the CE-MRA scan. As shown in FIG. 21, the monitor region determination unit 1930 includes a scan lead time determination unit 2110, a scan lead distance determination unit 2120 and a boundary determination unit 2130. The scan lead time determination unit 2110 is configured to determine a scan lead time, and includes a sequence switching time determination unit 2111, a k-space centric-filling time determination unit 2112 and a summation unit 2113. The sequence switching time determination unit 2111 is configured to determine a sequence switching time according to the type of a sequence for the CE-MRA scan. The k-space centric-filling time determination unit 2112 is configured to determine a k-space centric-filling time according to the type of a k-space filling method. The summation unit 2113 is configured to sum the sequence switching time and the k-space centric-filling time as a scan lead time. The scan lead distance determination unit 2120 is configured to calculate a scan lead distance according to the blood flow velocity and the scan lead time. The boundary determination unit 2130 is configured to determine a downstream boundary of the monitor region in the blood flow direction of the target vessel according to the scan lead distance and the CE-MRA scan region. Similarly, the downstream boundary of the monitor region is set at a position that the downstream boundary of the CE-MRA scan region in the blood flow direction is to reach after being moved the scan lead distance in a direction inverse to the blood flow direction.

In addition, the monitor region determination unit may be further configured to set the monitor region in the plane where a CE-MRA scan region is located. This is the same as in the prior art and needs not be described here in detail.

More detailed operations of each unit in the apparatus according to the embodiments of the present invention can be understood with reference to related description on the method according to the embodiments of the present invention and is therefore not repeated here.

The method and apparatus for determining a trigger timing of a CE-MRA scan according to the embodiments of the present invention determine the trigger timing by taking a blood flow velocity into consideration, and can determine the trigger timing of the CE-MRA scan automatically and accurately.

As an example, the respective steps of the method for determining a trigger timing of a CE-MRA scan and the respective modules and/or units of the apparatus according to the embodiments of the present invention may be implemented as software, firmware, hardware or a combination thereof in a CE-MRA system, and serve as a part of the CE-MRA system. As another example, the respective steps of the above-described method and the respective modules and/or units of the above-described apparatus may be implemented as an apparatus separately from a CE-MRA system. The specific means or approaches that may be used in configuring the modules and units in the above-described apparatus through software, firmware, hardware or any combination thereof are well known to those skilled in the art and therefore will not be repeatedly described.

As an example, the steps of the above-described method and the modules and/or units of the above-described apparatus may be implemented as software, firmware, hardware or a combination thereof. In the case where the steps of the above-described method and the modules and/or units of the above-described apparatus are implemented through software or firmware, a program constituting the software for implementing the above-described method may be installed in a computer (e.g. the general computer 2200 shown in FIG. 22) with a dedicate hardware structure from a storage medium or a network, and the computer, when installed with various programs, is capable of perform various functions.

Figure 22:
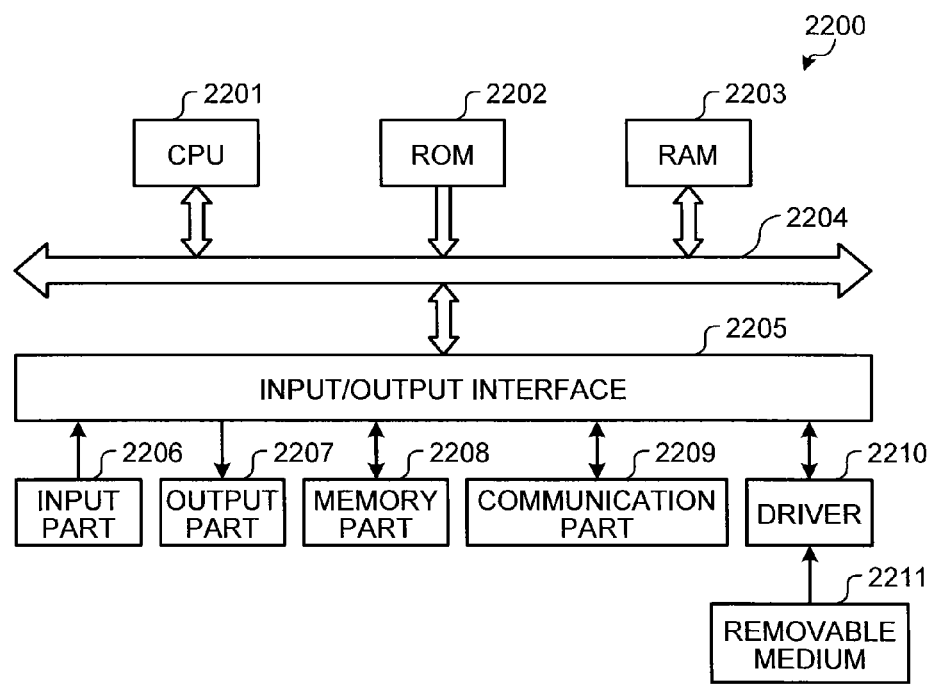
FIG. 22 is an exemplary block diagram illustrating the structure of a computer capable of implementing the embodiments/examples of the present invention.

In FIG. 22, a central processing unit (i.e. CPU) 2201 executes various processes according to the programs stored in a read-only memory (ROM) 2202 or programs loaded to a random access memory (RAM) 2203 from a storage part 2208. Data needed by the CPU 2201 in executing the various processes are also stored in the RAM 2203 as required. The CPU 2201, the ROM 2202 and the RAM 2203 are connected with each other via a bus 2204. An input/output interface 2205 is also connected to the bus 2204.

The following parts are connected to the input/output (I/O) interface 2205: an input part 2206 (including a keyboard, a mouse and etc.), an output part 2207 (including a display such as a cathode-ray tube (CRT) or a liquid crystal display (LCD), and a speaker, etc.), the storage part 2208 (including a hard disk, etc.), and a communication part 2209 (including a network interface card such as an LAN card, a MODEM and etc.). The communication part 2209 executes communication processing via a network such as the Internet. A driver 2210 can also be connected to the input/output interface 2205 as required. A removable medium 2211 such as a magnetic disk, an optical disk, a magneto-optical disk or a semiconductor memory can be mounted on the driver 2210 as required, such that the computer program read out therefrom is installed into the storage part 2208 as required.

In the case that the above series of processes are implemented by software, a program constituting the software is installed from a network such as the Internet or from a storage medium such as the removable medium 2211.

It is to be understood by those skilled in the art that such storage medium is not limited to the removable medium 2211 storing programs therein and distributing the programs to a user(s) dependently from a device. Examples of the removable medium 2211 include a magnetic disk (including a Floppy Disk (registered trademark)), an optical disk (including a Compact Disk-Read Only Memory (CD-ROM) and a Digital Versatile Disc (DVD)), a magneto-optical disk (including a Microdisk (MD) (registered trademark)) and a semiconductor memory. Alternatively, the storage medium can be the ROM 2202, a hard disk contained in the storage part 2208, etc., in which programs are stored and which is distributed to a user(s) along with a device the storage medium is contained in.

The present invention further provides a program product in which computer-readable instruction codes are stored. The instruction codes, when read and executed by a machine, can execute the methods according to the embodiments of the present invention.

Correspondingly, the storage medium for carrying the program product storing machine-readable instruction codes is also incorporated in the disclosure of the present invention. The storage medium includes, but is not limited to, a flexible disk, an optical disk, a magneto-optical disk, a storage card and a storage stick.

In the exemplary embodiments above, the examples are explained in which the apparatus 1100 performs the various types of processes described above; however, the exemplary embodiments are not limited to these examples. For example, another arrangement is acceptable in which a computer comprising in an MRI apparatus performs the various types of processes described above.

Figure 23:
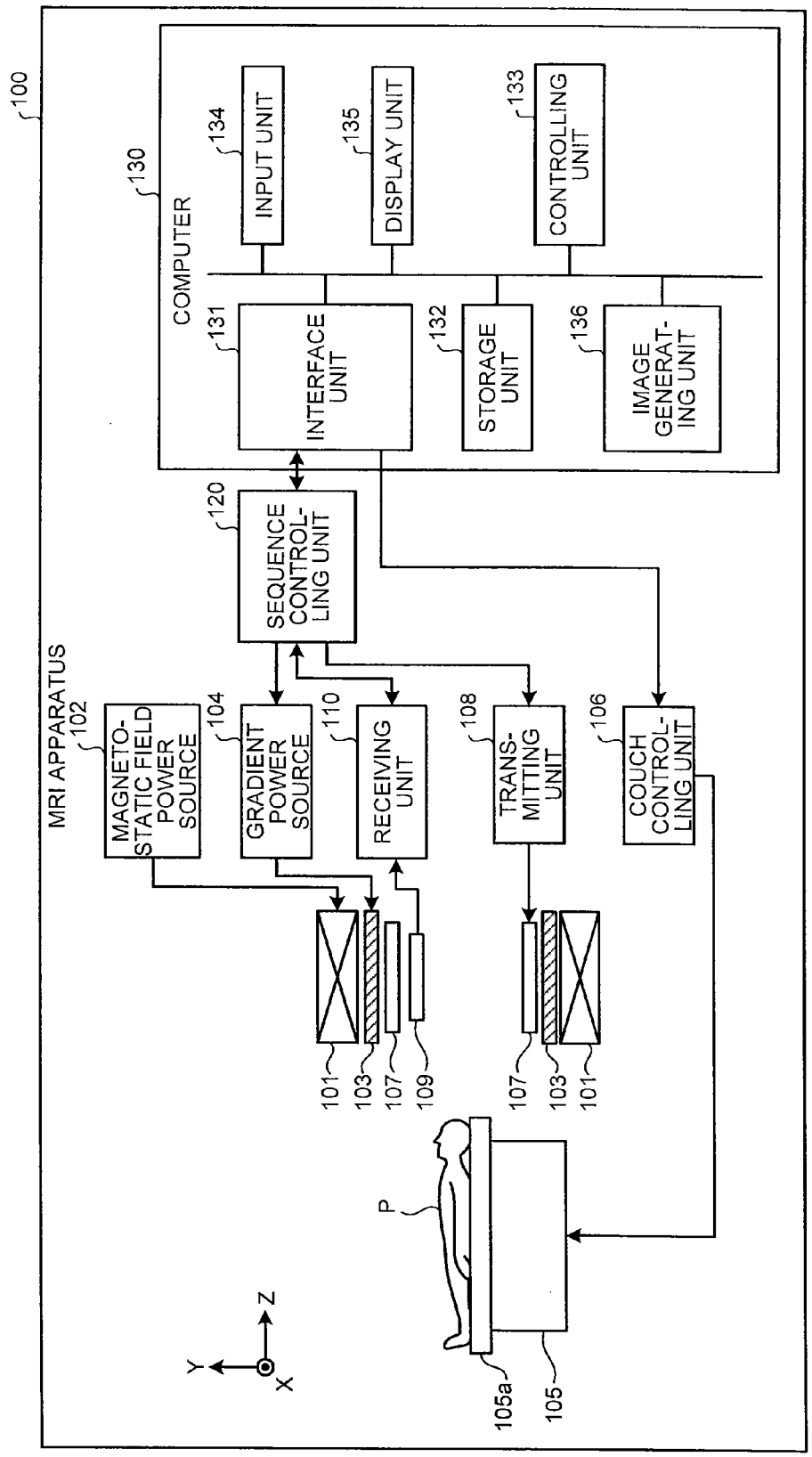
FIG. 23 is a functional block diagram depicting a configuration of an MRI apparatus.

FIG. 23 is a functional block diagram depicting a configuration of an MRI apparatus 100. As shown in FIG. 23, the MRI apparatus 100 includes a magnetostatic field magnet 101, a magnetostatic field power source 102, a gradient coil 103, a gradient power source 104, a couch 105, a couch controlling unit 106, a transmission coil 107, a transmitting unit 108, a reception coil 109, a receiving unit 110, a sequence controlling unit 120, and a computer 130. A subject P (e.g., a human body) is not included in the MRI apparatus 100. The configuration shown in FIG. 23 is merely an example. For instance, the functional units included in the sequence controlling unit 120 and the computer 130 may be configured as being integrated together or separated, as necessary.

The magnetostatic field magnet 101 is a magnet formed in the shape of a hollow circular cylinder and generates a magnetostatic field in the space on the inside thereof. The magnetostatic field magnet 101 may be configured by using, for example, a superconductive magnet. The magnetostatic field magnet 101 is configured to be excited by receiving a supply of electric current from the magnetostatic field power source 102. The magnetostatic field power source 102 supplies the electric current to the magnetostatic field magnet 101. Alternatively, the magnetostatic field magnet 101 may be configured by using a permanent magnet. In that situation, the MRI apparatus 100 does not necessarily have to include the magnetostatic field power source 102. It is also acceptable to provide the magnetostatic field power source 102 separately from the MRI apparatus 100.

The gradient coil 103 is a coil formed in the shape of a hollow circular cylinder and is disposed on the inside of the magnetostatic field magnet 101. The gradient coil 103 is formed by combining three coils corresponding to X-, Y-, and Z-axes that are orthogonal to one another. These three coils individually receive a supply of electric current from the gradient power source 104 and generate gradient magnetic fields of which the magnetic field intensities change along the X-, Y-, and Z-axes. The gradient magnetic fields on the X-, Y-, and Z-axes that are generated by the gradient coil 103 are, for example, a slice encoding gradient magnetic field $G_{SE}$ (or a slice selecting gradient magnetic field $G_{SS}$), a phase encoding gradient magnetic field $G_{PE}$, and a frequency encoding gradient magnetic field $G_{RO}$, respectively. The gradient power source 104 supplies electric current to the gradient coil 103.

The couch 105 includes a couchtop 105a on which the subject P is placed. Under control of the couch controlling unit 106, while the subject P is placed thereon, the couchtop 105a is inserted into the hollow (i.e., an image taking opening) of the gradient coil 103. Normally, the couch 105 is provided so that the longitudinal direction thereof extends parallel to the central axis of the magnetostatic field magnet 101. Under control of the computer 130, the couch controlling unit 106 drives the couch 105 so that the couchtop 105a moves in the longitudinal direction and in an up-and-down direction.

The transmission coil 107 is disposed on the inside of the gradient coil 103 and generates a radio-frequency magnetic field by receiving a supply of a Radio Frequency (RF) pulse from the transmitting unit 108. The transmitting unit 108 supplies the RF pulse corresponding to a Larmor frequency, which is determined by the type of a target atom and the intensity of the magnetic field, to the transmission coil 107.

The reception coil 109 is disposed on the inside of the gradient coil 103 and receives Magnetic Resonance (MR) signals emitted from the subject P due to an influence of the radio-frequency magnetic field. When having received the MR signals, the reception coil 109 outputs the received MR signals to the receiving unit 110.

The transmission coil 107 and the reception coil 109 described above are merely examples. It is acceptable to use one or more in combination selected from among a coil having only a transmitting function, a coil having only a receiving function, and a coil having a transmitting and receiving function.

The receiving unit 110 detects the MR signals being output from the reception coil 109 and generates MR data based on the detected MR signals. More specifically, the receiving unit 110 generates the MR data by applying a digital conversion to the MR signals being output from the reception coil 109. Further, the receiving unit 110 transmits the generated MR data to the sequence controlling unit 120. The receiving unit 110 may be provided on a gantry device side where the magnetostatic field magnet 101, the gradient coil 103, and like are provided.

The sequence controlling unit 120 performs an image taking process on the subject P, by driving the gradient power source 104, the transmitting unit 108, and the receiving unit 110, based on sequence information transmitted from the computer 130. In this situation, the sequence information is information that defines a procedure for performing the image taking process. The sequence information defines, for example, the intensity of the electric current to be supplied by the gradient power source 104 to the gradient coil 103 and the timing with which the electric current is to be supplied; the strength of the RF pulse to be supplied by the transmitting unit 108 to the transmission coil 107 and the timing with which the RF pulse is to be applied; and the timing with which the MR signals are to be detected by the receiving unit 110. The sequence controlling unit 120 is configured by using, for example, an integrated circuit such as an Application Specific Integrated Circuit (ASIC) or a Field Programmable Gate Array (FPGA), or an electronic circuit such as a Central Processing Unit (CPU) or a Micro Processing Unit (MPU).

When the sequence controlling unit 120 has received the MR data from the receiving unit 110, as a result of driving the gradient power source 104, the transmitting unit 108, and the receiving unit 110 and taking the image of the subject P, the sequence controlling unit 120 transfers the received MR data to the computer 130.

The computer 130 exercises overall control of the MRI apparatus 100 and generates an MR image, for example. The computer 130 includes an interface unit 131, a storage unit 132, the controlling unit 133, an input unit 134, a display unit 135, and an image generating unit 136.

The interface unit 131 transmits the sequence information to the sequence controlling unit 120 and receives the MR data from the sequence controlling unit 120. When having received the MR data, the interface unit 131 stores the received MR data into the storage unit 132. The MR data stored in the storage unit 132 is arranged into a k-space by the controlling unit 133. As a result, the storage unit 132 stores therein k-space data corresponding to a plurality of channels.

The storage unit 132 stores therein, for example, the MR data received by the interface unit 131, the k-space data arranged in the k-space by the controlling unit 133, and image data generated by the image generating unit 136. For example, the storage unit 132 is configured by using a semiconductor memory element such as a Random Access Memory (RAM) or a flash memory, a hard disk, an optical disk, or the like.

The input unit 134 receives various types of instructions and inputs of information from an operator. The input unit 134 is configured by using a pointing device such as a mouse or a trackball, a selecting device such as a mode changing switch, and/or an input device such as a keyboard. Under control of the controlling unit 133, the display unit 135 displays various types of information such as spectrum data and the image data. The display unit 135 is configured by using, for example, a display device such as a liquid crystal display device.

The controlling unit 133 exercises overall control of the MRI apparatus 100. More specifically, the controlling unit 133 controls the image taking process by generating the sequence information based on an image taking condition input from the operator via the input unit 134 and transmitting the generated sequence information to the sequence controlling unit 120. Further, the controlling unit 133 controls the image generating process performed based on the MR data and controls the display process realized by the display unit 135. Further, the controlling unit 133 reads the MR data generated by the receiving unit 110 from the storage unit 132 and arranges the read MR data into the k-space. For example, the controlling unit 133 is configured by using an integrated circuit such as an ASIC or an FPGA, or an electronic circuit such as a CPU or an MPU.

The image generating unit 136 reads the k-space data arranged in the k-space by the controlling unit 133 from the storage unit 132 and generates the MR image by applying a reconstructing process such as a Fourier transform to the read k-space data.

In the above description of the specific embodiments of the present invention, features described and/or illustrated with respect to one embodiment can be used in one or more other embodiments in an identical or similar manner, be combined with features in other embodiments, or replace features in other embodiments.

It should be emphasized that, the term "comprise/include", as used in the present description, refers to the presence of features, sections, steps or components, but does not exclude the presence or addition of one or more other features, sections, steps or components.

In the above embodiments and examples, the steps and/or units are represented with a reference sign consisting of numbers. It should be understood by those of ordinary skill of the art that the reference signs are merely intended to facilitate description and drawing depiction, but are not to be construed as indicating the orders of the steps and/or units nor a limitation on any other aspect.

Furthermore, the methods of the present invention are not limited to being executed in the temporal orders as described in the specification, but can also be executed in other temporal order, in parallel or separately. Therefore, the execution orders of the methods described in the present specification do not constitute a limitation to the technical scope of the present invention.

Although the present invention has been disclosed with reference to descriptions for the specific embodiments of the present invention, it should be understood that all of the above mentioned embodiments and examples are illustrative instead of limiting. Those skilled in the art can devise various modifications, improvements or equivalents for the present invention, within the spirit and scope of the appended claims. The modifications, improvements or equivalents should also be considered as being included in the protection scope of the present invention.

What is claimed is:

1. An apparatus for performing a Contrast Enhanced Magnetic Resonance Angiography (CE-MRA) scan, comprising:
   processing circuitry configured to
   obtain a blood flow velocity of a target vessel; and
   determine, prior to the CE-MRA scan, a trigger timing for performing the CE-MRA scan on a CE-MRA scan region; and
   a magnetic resonance imaging device configured to perform the CE-MRA scan according to the determined trigger timing,
   wherein the processing circuitry is further configured to:
   cause the magnetic resonance imaging device to perform a monitoring scan;
   determine a sequence switching time according to a specific type of a sequence for the CE-MRA scan as a scan lead time, wherein the sequence switching time is a time needed for switching from the monitoring scan to the CE-MRA scan of the specific type;
   calculate a scan lead distance according to the blood flow velocity and the scan lead time, and determine a trigger position based on the scan lead distance and the CE-MRA scan region;
   calculate, according to the blood flow velocity, a time needed for a contrast agent in the target vessel to flow to the trigger position from a current position of the contrast agent in the target vessel, which is detected through the monitoring scan, as a residual trigger time;
   perform a modular calculation on the residual trigger time with an inter-frame time interval of the monitoring scan as a modulus; and
   start a residual trigger time countdown when a remainder resulting from the modular calculation is not zero and when a same number of frames as a quotient resulting from the modular calculation have been scanned through the monitoring scan, and determine the trigger timing as a time at which it is determined, through the residual trigger time countdown, that a time equal to the remainder resulting from the modular calculation has elapsed.

* * * * *